United States Patent
Koibuchi et al.

(10) Patent No.: US 6,830,905 B2
(45) Date of Patent: Dec. 14, 2004

(54) GLUTAMINASE, ITS GENE AND A METHOD OF PRODUCING IT

(75) Inventors: Kyoko Koibuchi, Kawasaki (JP); Hiroaki Nagasaki, Kawasaki (JP); Ari Yuasa, Kawasaki (JP); Jiro Kataoka, Kawasaki (JP); Katsuhiko Kitamoto, Ushiku (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/262,083

(22) Filed: Oct. 2, 2002

(65) Prior Publication Data

US 2003/0170670 A1 Sep. 11, 2003

Related U.S. Application Data

(62) Division of application No. 09/674,507, filed as application No. PCT/JP99/02455 on May 12, 1999, now abandoned.

(30) Foreign Application Priority Data

| May 15, 1998 | (JP) | 10-134080 |
| Sep. 11, 1998 | (JP) | 10-258974 |
| Oct. 14, 1998 | (JP) | 10-292443 |
| Mar. 30, 1999 | (JP) | 11-89157 |

(51) Int. Cl.$^7$ .................. C12P 13/14; C12N 9/80; C07H 21/04

(52) U.S. Cl. .................. 435/110; 435/228; 435/227; 435/253.3; 435/253.33; 435/254.3; 435/320.1; 536/23.2; 536/23.7

(58) Field of Search .................. 435/110, 227, 435/228, 252.3, 252.33, 254.3, 320.1, 229; 536/23.2, 23.7; 424/94.6

(56) References Cited

PUBLICATIONS

Yano et al. "Purification and Properties of Glutaminase from *Aspegillus oryzae*" J. Ferment. Tech. 1988, 66(2), 137–143.*
T. Yano et al., Agricultural and Biological Chemistry, vol. 55, No. 2, XP–001057982, pp. 387–391, "Production and Localization of Enzymes on Soft Gel Cultivation", 1991.
K. Koibuchi et al., Applied Microbiology and Biotechnology, vol. 54, No. 1, XP–002191327, pp. 59–68, "Molecular Cloning and Characterization of a Gene Encoding Glutaminase from *Aspergillus Oryzae*", Jul. 2000.

* cited by examiner

*Primary Examiner*—Nashaat T. Nashed
(74) *Attorney, Agent, or Firm*—Oblon, Spivak, McClelland, Maier & Neustadt, P.C.

(57) ABSTRACT

Glutaminase is purified from an *Aspergillus oryzae*, its partial amino acid sequence is determined, a partial sequence of glutaminase gene is obtained by PCR based on the obtained information, and DNA fragments containing glutaminase gene from *Aspergillus oryzae* genomic library and cDNA library, and *Aspergillus nidulans* genomic library hybridization using the partial sequence as a probe.

22 Claims, No Drawings

GLUTAMINASE, ITS GENE AND A METHOD OF PRODUCING IT

This application is a Division of application Ser. No. 09/674,507 Filed on Nov. 15, 2000 now abandoned, allowed, which was filed as International Application PCT/JP99/02455 filed May 12, 1999.

TECHNICAL FIELD

The present invention relates a novel glutaminase and a gene encoding the same. The glutaminase of the present invention can be utilized as an enzyme for food processing to convert glutamine into glutamic acid exhibiting stronger "umami" taste (umami).

BACKGROUND ART

For the production of soy sauce, miso, and other natural seasonings containing protein hydrolysate products, koji mould (filamentous fungus belonging to the genus Aspergillus) has been utilized. For example, soy sauce is produced through two process steps of koji-making and fermentation. In the koji-making step, the starting material is principally degraded by enzymes produced by koji mould. In such a process, it is important to increase the amount of glutamic acid among various tasteful materials in order to obtain stronger umami of soy sauce.

Glutamic acid is produced through two kinds of pathways. The first is the liberation of glutamic acid from protein caused by protease and peptidase. The second is generation of glutamic acid through hydrolysis of glutamine catalyzed by glutaminase (glutamine amidohydrolase).

In the production of soy sauce, liberation ratio of glutamic acid relative to its content in the starting material is not so high, and this is considered to be due to insufficient glutaminase activity of koji mould. Therefore, breeding of strains exhibiting high activities of protease and glutaminase through cell fusion of high protease activity strain and high glutaminase activity strain in solid koji has also been attempted (Ushijima, S. et al., Agric. Biol. Chem., 51 (4), 1051 (1987), Japanese Patent Publication (KOKOKU) No. Hei 3-73271/1992).

As for glutaminase, those derived from various bacteria and animals have been well investigated (Wakayama, M. et al., J. Ferment. Bioeng., 82, No.6, 592–597 (1996), Chung-Bok, Mi, et al., Biochem. J., 324, 193–200 (1997), Duran, S. et al., Biochem. Genet., 34, 453–465 (1996)). On the other hand, investigation about glutaminase of koji mould had been retarded, but extracellular glutaminase and intracellular glutaminase have been purified from one strain of *Aspergillus oryzae*, and they have been characterized (Yano, T. et al., J. Ferment. Technol., Vol. 66, No. 2, 137–143 (1988)). These glutaminases have a molecular weight of about 113,000, and substantially similar properties.

Further, there have been determined an amino acid sequence of N-terminal region of glutaminase derived from *Aspergillus oryzae* HG strain (Fukuoka Industrial Technology Center, Institute of Biology and Food, Research Summary of 1996 (199)), and amino acid sequence within N-terminal region of glutaminase derived from *Aspergillus oryzae* (Food Research Institute, Aichi Prefectural Government, Japan, Annual Report of 1995 (Research Report) pp.3–4, (1996)) for purified glutaminases.

Meanwhile, because koji mould is excellent in the ability for secreting extracellular proteins, it has been attracted attention as a host for the production of recombinant proteins, and practically used for some enzymes.

DISCLOSURE OF THE INVENTION

As described above, koji mould has already afforded results as a material for genetic recombination technology, and its glutaminase has also been investigated to some extent. However, it cannot be considered to be fully investigated, and its further investigation has been desired. In addition, any genes encoding glutaminase of koji mould have not been isolated.

The present invention has been accomplished in view of the aforementioned state of the art, and its object is to provide a gene encoding glutaminase derived from koji mould.

The present inventors successfully purified glutaminase from *Aspergillus oryzae*, determined its partial amino acid sequence, and isolated DNA coding for the glutaminase based on the obtained information, and thus the present invention has been completed. Further, they also succeeded in isolating DNA encoding glutaminase of *Aspergillus nidulans*.

That is, the present invention provides the followings:

(1) a protein defined in any of the following (A) to (D):

(A) a protein having an amino acid sequence represented by the amino acid numbers 1–670 of SEQ ID NO: 2 in Sequence Listing;

(B) a protein having an amino acid sequence represented by the amino acid numbers 1–669 of SEQ ID NO: 22 in Sequence Listing;

(C) a protein having an amino acid sequence represented by the amino acid numbers 1–670 of SEQ ID NO: 2 in Sequence Listing with substitution, deletion, insertion, addition or inversion of one or a plurality of amino acids, and having activity for catalyzing hydrolysis of glutamine to glutamic acid and ammonia;

(D) a protein having an amino acid sequence represented by the amino acid numbers 1–669 of SEQ ID NO: 22 in Sequence Listing with substitution, deletion, insertion, addition or inversion of one or a plurality of amino acids, and having activity for catalyzing hydrolysis of glutamine to glutamic acid and ammonia;

(2) a DNA which encodes a protein defined in any of the following (A) to (D):

(A) a protein having an amino acid sequence represented by the amino acid numbers 1–670 of SEQ ID NO: 2 in Sequence Listing;

(B) a protein having an amino acid sequence represented by the amino acid numbers 1–669 of SEQ ID NO: 22 in Sequence Listing;

(C) a protein having an amino acid sequence represented by the amino acid numbers 1–670 of SEQ ID NO: 2 in Sequence Listing with substitution, deletion, insertion, addition or inversion of one or a plurality of amino acids, and having activity for catalyzing hydrolysis of glutamine to glutamic acid and ammonia;

(D) a protein having an amino acid sequence represented by the amino acid numbers 1–669 of SEQ ID NO: 22 in Sequence Listing with substitution, deletion, insertion, addition or inversion of one or a plurality of amino acids, and having activity for catalyzing hydrolysis of glutamine to glutamic acid and ammonia;

(3) the DNA of (2) which is a DNA defined in any of the following (a) to (d):

(a) a DNA which contains nucleotide sequences represented by the nucleotide numbers 1174–1370, 1446–1741, 1800–2242, 2297–2880, 2932–3134, 3181–3324, 3380–3515, 3562–3628 of the nucleotide sequence or SEQ ID NO: 1 in Sequence Listing in this order;

(b) a DNA which contains nucleotide sequences represented by the nucleotide numbers 1807–2000, 2061–2353, 2412–2854, 2915–3498, 3554–3756, 3806–3949, 3996–4131, 4180–4246 of the nucleotide sequence of SEQ ID NO: 21 in Sequence Listing in this order;

(c) a DNA which hybridizes with the DNA of (a) under a stringent condition, and encodes a protein having activity for catalyzing hydrolysis of glutamine to glutamic acid and ammonia;

(d) a DNA which hybridizes with the DNA of (b) under a stringent condition, and encodes a protein having activity for catalyzing hydrolysis of glutamine to glutamic acid and ammonia;

(4) the DNA of (2) which has a nucleotide sequence shown in SEQ ID NO: 1 or SEQ ID NO: 17;

(5) the DNA of (3) which has a nucleotide sequence shown in SEQ ID NO: 21 or SEQ ID NO: 25;

(6) a recombinant vector comprising the DNA of (2) inserted in a vector;

(7) a transformant of microorganism introduced with the DNA of (2) in such a manner that the DNA can be expressed to produce glutaminase;

(8) the transformant of (7) which is derived From a filamentous fungus or bacterium belonging to the genus *Escherichia*; and (9) a method for producing glutaminase which comprises cultivating the transformant of (7) in a culture medium to produce glutaminase in the culture.

The term "glutaminase activity" used in this specification means activity for catalyzing hydrolysis of L-glutamine to L-glutamic acid and ammonia, and the activity may include activity for catalyzing hydrolysis of D-glutamine to D-glutamic acid and ammonia. The activity may also include activities for catalyzing hydrolysis of L-glutamine to L-glutamic acid and ammonia, and D-glutamine into D-glutamic acid and ammonia, and activity for catalyzing transfer reaction or hydrolysis reaction of glutamyl group of L-γ-glutamyl compounds. In the present specification two embodiments are disclosed as the glutaminase of the present invention. One or both of the embodiments, or equivalents thereof may occasionally be referred to as glutaminase of the present invention. Also, the DNA which encodes the glutaminase of the present invention may occasionally be referred to as glutaminase gene.

The glutaminase of the present invention is distinguished from known glutaminases derived from koji mould based on enzymological properties, and therefore it is considered a novel glutaminase.

The present invention will be explained in detail hereinafter.

<1> Glutaminase of the Present Invention

The glutaminase of the present invention can be obtained from culture of *Aspergillus oryzae* RIB40 (ATCC 42149) by purifying it, for example, as follows.

*Aspergillus oryzae* RIB40 (ATCC 42149) is cultured with wheat bran, and the obtained bran koji is immersed in a buffer solution to prepare a crude enzyme extract. This crude enzyme extract is subjected to freeze and thawing, and insoluble fractions are removed to obtain a supernatant. This supernatant is subjected to ammonium sulfate fractionation to obtain a fraction not precipitated with 55% saturated ammonium sulfate but precipitated with 85% saturated ammonium sulfate. The ammonium sulfate is removed from this fraction, and resultant can further be fractionated by anion exchange chromatography, hydrophobic chromatography, and gel filtration chromatography to provide purified glutaminase. As resins for the chromatographies, there are exemplified DEAE-TOYOPEARL (Tosoh) for the anion exchange chromatography, Phenyl Sepharose (Pharmacia) for the hydrophobic chromatography, and Superdex (Pharmacia) for the gel filtration chromatography. These purification procedures may be repeatedly performed.

In each step for purification or glutaminase, the desired fraction is selected based on the glutaminase activity. The glutaminase activity can be determined by a modified version of the method of Hartaran (Hartman, S. C., J. Biol. Chem., 243, 853–863 (1968), the hydroxamate method).

Enzymological properties of the glutaminase obtained from bran koji of *Aspergillus oryzae* RIB40 (ATCC 42149) as described above are shown in Table 1 together with enzymological properties of known glutaminases, one derived from of *Aspergillus oryzae* (Yano, T. et al., J. Ferment. Technol., Vol. 66, No. 2, 137–143 (1988)), and one derived from *Bacillus subtilis* (Shimazu, H. et al., J. Brew. Soc. Japan, 86, No. 6, 441–446 (1991)).

TABLE 1

Enzymological properties of glutaminase of the present invention and known glutaminases

| | Glutaminase of The present invention | Derived from A. Oryzae Yano, T. et al. | Derived from B. subtilis Shimazu, H. et al. |
|---|---|---|---|
| Molecular weight | 82,090[1] | 113,000[2] | 55,000 |
| Optimum pH | pH 9 | pH 9 | PH 6 |
| PH stability | pH 7 | pH 9 | PH 5–8 |
| Optimum temperature | 37–45° C. | 45° C. | 50° C. |
| Temperature Stability | 0–45° C. | 0–37° C. | 0–45° C. |
| Salt Tolerance[3] | 50% at 5% NaCl 20% at 18% NaCl | 50% at 5% NaCl 10% at 18% NaCl | 100% at 10% NaCl 85% or more at 25% NaCl |
| Substrate Specificity[4] | L-Gln (100%) D-Gln (106%) L-Asn (97%) D-Asn (104%) | L-Gln (100%) D-Gln (2%) L-Asn (0%) D-Asn (0%) | L-Gln (100%) D-Gln (67%) L-Asn (0%) D-Asn (0%) |
| Reaction Specificity | γ-Glu-p-NA | γ-Glu-p-NA | γ-Glu-p-NA (not tested) |
| Transfer[5] | (10%) | (0%) | (0%) |
| Hydrolysis[6] | (16%) | (131%) | (0%) |
| Km value | $1.24 \times 10^{-3}$ M | $9.6 \times 10^{-5}$ M | $6.4 \times 10^{-4}$ M |

[1]Measured by MALDI-TOFMS
[2]Measured by gel filtration
[3]Relative values based on the activity in the absence of NaCl that is defined as 100%
[4]Relative values of activity for D-glutamic acid (D-Gln) based on the activity for L-glutamic acid (L-Gln) that is defined as 100%
[5]L-γ-glutamyl-p-nitroanilide + GlyGlu → L-γ-glutamyl-GlyGlu + p-nitroanilide
[6]L-γ-glutamyl-p-nitroanilide + H$_2$O → L-glutamate + p-nitroanilide Based on the marked differences in enzymological properties shown above, in particular in the substrate specificity, the glutaminase of the present invention is concluded to be novel, and different from the known glutaminase derived from *Aspergillus oryzae*.

While the glutaminase of the present invention can be obtained by purifying it from culture of *Aspergillus oryzae* as described above, it can also be produced by expression of glutaminase gene of *Aspergillus oryzae* described below in a suitable host as will be described hereinafter.

As will be described hereinafter, the glutaminase derived from *Aspergillus oryzae* is expected to have the amino acid sequence represented by the amino acid numbers 1–670 in SEQ ID NO: 2 based on the nucleotide sequence of glutaminase gene. The molecular weight calculated from this amino acid sequence is about 76,000, and from its comparison with the value of molecular weight measured by MALDI-TOFMS, the glutaminase of the present invention is expected to be a glycoprotein.

The glutaminase of another embodiment of the present invention is derived from *Aspergillus nidulans*. The glutaminase derived from *Aspergillus nidulans* may be produced by purifying from a culture of *Aspergillus nidulans* in the same manner as described above, or expressing the glutaminase gene of *Aspergillus nidulans* in an appropriate host. The glutaminase derived from *Aspergillus nidulans* has deduced amino acid sequence represented by the amino acid numbers 1–669 of SEQ ID NO: 22 from the nucleotide sequence of the glutaminase gene.

As for the glutaminase of the present invention, so long as it has activity for catalyzing hydrolysis of glutamine to glutamic acid and ammonia, the aforementioned amino acid sequence may have substitution, deletion, insertion, addition or inversion of one or a plurality of amino acids.

The present invention also provides, as an embodiment of the glutaminase of the present invention, glutaminase of *Aspergillus nidulans* having the amino acid sequence shown in SEQ ID NO: 22. This glutaminase can be produced by purifying it from culture of *Aspergillus nidulans* in a manner similar to that described above, or by expression of glutaminase gene of *Aspergillus nidulans* in a suitable host.

<2> DNA of the Present Invention

The DNA of the present invention can be obtained from genomic DNA of *Aspergillus oryzae* RIB40 (ATCC 42149), for example, as follows.

A partial amino acid sequence of the purified glutaminase is determined, and oligonucleotide primers for PCR (polymerase chain reaction) are synthesized based on the obtained information of the amino acid sequence to perform PCR using genomic DNA prepared from fungal cells of *Aspergillus oryzae* RIB40 (ATCC42149) as template. Partial sequences determined in the working examples of the present invention to be described hereinafter are shown in SEQ ID NOS: 3–10. Among these sequences, SEQ ID NO: 3 is an N-terminal amino acid sequence of the glutaminase protein, and the other sequences are internal amino acid sequences of the glutaminase. The amino acid sequences shown in SEQ ID NOS: 5 and 8 were not present in the amino acid sequence of glutaminase expected from the glutaminase gene. The third Ala and the ninth Thr in the amino acid sequence shown in SEQ ID NO: 7 were replaced by Thr and Ser respectively in the amino acid sequence of glutaminase expected from the glutaminase gene, and it was considered that they were reading errors in peptide sequencer.

The genomic DNA can be obtained by the method of Gomi (Gomi, K. et al., J. Gen. Appl. Microbiol., 35, 225 (1989)).

By using oligonucleotides having nucleotide sequences shown in SEQ ID NO: 11 and SEQ ID NO: 12 of Sequence Listing as the primers, a DNA fragment of about 230 bp can be obtained by the aforementioned PCR.

Then, plaque hybridization is performed for a genomic DNA library of *Aspergillus oryzae* RIB40 (ATCC 42149) utilizing λ phage as a vector by using the DNA. fragment amplified by PCR as a DNA probe to obtain positive clones.

Within the cloned fragment obtained as described above, nucleotide sequence of a portion having a length of about 4 kb within a region having about 4.8 kb (XHoI fragment) is determined, and the result is shown in SEQ ID NO: 1 of Sequence Listing. In SEQ ID NO: 1, the amino acid sequence encoded by nucleotides of the nucleotide numbers 1234–1284 corresponds to the amino acid sequence of the amino acid numbers 1–17 in the N-terminal amino acid sequence of the glutaminase protein shown in SEQ ID NO: 3. The amino acid sequences shown in SEQ ID NOS: 4, 6, 7, 9 and 10 respectively correspond to the amino acid sequences encoded by nucleotides of the nucleotide numbers 2618–2647, 2762–2803, 2804–2848, 2957–2986, and 2576–2605 of the nucleotide sequence shown in SEQ ID NO: 1.

From the above, it is clear that DNA having the nucleotide sequence shown in SEQ ID NO: 1 is a glutaminase gene.

From the comparison of the nucleotide sequence shown in SEQ ID NO: 1 and the nucleotide sequence of glutaminase cDNA to be described hereinafter, it was found that the nucleotide sequence of SEQ ID NO: 1 contained 8 exons (nucleotide numbers 1174 or 1135–1370, 1446–1741, 1800–2242, 2297–2880, 2932–3134, 3181–3324, 3380–3515, and 3562–3628), and these exons encoded an amino acid sequence comprised of 690 residues. This amino acid sequence is shown in SEQ ID NOS: 1 and 2. From the comparison of this amino acid sequence and the amino acid sequence of the N-terminal of the glutaminase protein shown in SEQ ID NO: 3, it is estimated that the sequence of the amino acid numbers −20 to −1 is a signal peptide, and the sequence of the amino acid numbers 1–670 is the mature protein in SEQ ID NO: 2. While the initiation codon is estimated to be ATG of the nucleotide numbers 1174–1176, the possibility that it consists of ATG at the nucleotide numbers 1135–1138 cannot be denied.

From the above, it is strongly suggested that DNA having the nucleotide sequence shown in SEQ ID NO: 1 contains a promoter and a region encoding glutaminase (including signal peptide).

The DNA of the present invention may be DNA of the nucleotide sequence shown in SEQ ID NO: 1 of which introns are removed, i.e., DNA comprising nucleotide sequences of nucleotide numbers 1174–1370, 1446–1741, 1800–2242, 2297–2880, 2932–3134, 3181–3324, 3380–3515 and 3562–3628 in this order, so long as it encodes the glutaminase of the present invention. Such DNA can be obtained, for example, as cDNA of the aforementioned glutaminase gene.

Glutaminase cDNA can be obtained, for example, from a cDNA library prepared from poly(A) RNA of *Aspergillus oryzae* by hybridization which utilizes DNA having the nucleotide sequence of SEQ ID NO: 1 or a part thereof (e.g., the aforementioned probe of about 230 bp).

Glutaminase cDNA can also be obtained by PCR utilizing oligonucleotides having the nucleotide sequences of SEQ ID NOS: 13 and 14 as primers, and by 3'-RACE utilizing oligonucleotides having the nucleotide sequences of SEQ ID NOS: 15 and 16 as primers. An exemplary nucleotide sequence of cDNA obtained from a highly glutaminase productive strain of *Aspergillus oryzae* is shown in SEQ ID NO: 17 of Sequence Listing. The amino acid sequence deduced from this nucleotide sequence is shown in SEQ ID NOS: 17 and 18. When the nucleotide sequence of this cDNA was compared with the sequence of the coding region in the genomic gene obtained in Example 2, they were identical except that "C" at the nucleotide number 54 of the cDNA (SEQ ID NO: 17) was "G" (nucleotide number 1227) in the genomic gene (SEQ ID NO: 1). This difference between the nucleotide sequences of the cDNA and the genomic gene is estimated to be due to difference of gene sequence between the strains.

The DNA of the present invention may be any one encoding glutaminase, and it includes, in addition to DNA having the nucleotide sequence shown in SEQ ID NO: 1 or SEQ ID NO: 17, those DNA of which unnecessary portions in 5' region have been removed. Depending on purpose of the use, it may be one encoding only the mature protein. DNA of which one or more codons encoding amino acids in the coding region are replaced with equivalent codons encoding the same amino acids is included in the DNA of the present invention. Further, the DNA of the present invention may be one encoding glutaminase having substitution, deletion, insertion, addition or inversion of one or a plurality of amino acids at one or a plurality of sites, so long as the activity of glutaminase is not degraded. The number of the amino acid meant by the expression "a plurality of" may vary depending on the location or kinds of amino acid residues in the three-dimensional structure of the glutaminase protein, but it may be usually 2–300, preferably 2–170, more preferably 2–50, most preferably 2–10.

As will be described hereinafter, the amino acid sequence of glutaminase of *Aspergillus oryzae* shown in SEQ ID NO: 2 and the amino acid sequence of glutaminase of *Aspergillus nidulans* shown in SEQ ID NO: 22 have about 73% of homology, and about 170 amino acid residues are different between them as for the mature protein portion.

DNA encoding a protein substantially the same as glutaminase such as those mentioned above can be obtained by modifying the nucleotide sequence of glutaminase gene, for example, by the site-specific mutagenesis so that amino acids should be substituted, deleted, inserted or added at a particular site. Such modified DNA as mentioned above may also be obtained by a conventionally known mutagenesis treatment. As such a mutagenesis treatment, there can be mentioned a method comprising treating DNA encoding glutaminase with hydroxylamine or the like in vitro, and a method comprising irradiating a bacterium belonging to the genus *Escherichia* with ultraviolet light, or treating it with a mutagenic agent conventionally utilized for mutagenesis such as N-methyl-N'-nitro-N-nitrosoguanidine (NTG), and nitrous acid.

The substitution, deletion, insertion, addition and inversion mentioned above include those due to difference among strains, and naturally occurring mutations.

DNA encoding a protein substantially the same as glutaminase can be selected by expressing DNA having mutations as described above in a suitable cell, and examining the expression product for glutaminase activity. DNA encoding a protein substantially the same as glutaminase can also be obtained by isolating DNA which hybridizes with DNA having any one of nucleotide sequences of nucleotide numbers 1174–1370, 1446–1741, 1800–2242, 2297–2880, 2932–3134, 3181–3324, 3380–3515, and 3562–3628 in the nucleotide sequence of SEQ ID NO: 1 in Sequence Listing, or DNA having the nucleotide sequence of the nucleotide numbers 1–2070 in the nucleotide sequence of SEQ ID NO: 17 under a stringent condition, and encodes a protein having the glutaminase activity. The term "stringent condition" herein used means a condition where so-called specific hybrids may be formed, but non-specific hybrids are not formed. While it is difficult to definitely define this condition numerically, examples of such condition include, for example, a condition where DNAs having high homology, e.g., homology of 65% or more may hybridize with each other, but DNAs having homology lower than that may not hybridize with each other, and a condition where hybridization is performed at a salt concentration corresponding to that of washing step of usual Southern hybridization, i.e., 1×SSC, 0.1% SDS, preferably 0.1×SSC, 0.1% SDS. Genes which hybridize under such a condition may also include those having a stop codon generated to interrupt the coding sequence, those having lost their activity due to mutation at the active center and the like, but they can easily be removed by ligating the genes to a commercially available active expression vector, and determining glutaminase activity by the method described hereinafter.

The DNA of the present invention can also be obtained from chromosome DNA or cDNA of microorganism of another species belonging to the genus *Aspergillus*, for example, *Aspergillus nidulans*. Specifically, it can be obtained from a chromosome DNA library of *Aspergillus nidulans*, for example, *Aspergillus nidulans* A26 strain by hybridization. A probe for the hybridization can be prepared by synthesizing oligonucleotide primers For PCR based on the aforementioned nucleotide sequence of the glutaminase gene of *Aspergillus oryzae*, and performing PCR using genome DNA prepared from cells of *Aspergillus nidulans*, e.g., *Aspergillus nidulans* A26 strain as template. As the primers for PCR, oligonucleotides having nucleotide sequences of SEQ ID NOS: 19 and 20 can be mentioned.

The nucleotide sequence and the amino acid sequence of the glutaminase gene of *Aspergillus nidulans* A26 obtained in the working examples to be described hereinafter in the manner described above are shown in SEQ ID NO: 21. The amino acid sequence is also shown in SEQ ID NO: 22. The homology between the glutaminase gene of *Aspergillus nidulans* and the glutaminase gene of *Aspergillus oryzae* was about 58% for the whole gene, about 68% for the coding region, and about 73% for the encoded amino acid sequence.

Glutaminase cDNA can also be obtained from a cDNA library prepared from poly(A) RNA of *Aspergillus nidulans* by, for example, PCR using oligonucleotides having nucleotide sequences SEQ ID NOS: 23 and 24. An exemplary nucleotide sequence of cDNA obtained from *Aspergillus nidulans* A26 is shown in SEQ ID NO: 25 of Sequence Listing. The amino acid sequence deduced From this nucleotide sequence is shown in SEQ ID NOS: 25 and 26.

The DNA of the present invention includes a DNA which encodes a protein having an amino acid sequence represented by the amino acid numbers 1–669 of SEQ ID NO: 22 in Sequence Listing with substitution, deletion, insertion, addition or inversion of one or a plurality of amino acids, and having activity for catalyzing hydrolysis of glutamine to glutamic acid and ammonia. The DNA of the present invention also includes a DNA which encodes a DNA which contains nucleotide sequences represented by the nucleotide numbers 1807–2000, 2061–2353 2353, 2412–2854, 2915–3498, 3554–3756, 3806–3949, 3996–4131, 4180–4246 of the nucleotide sequence of SEQ ID NO: 21 in Sequence Listing in this order, and a DNA which hybridizes with the aforementioned DNA under a stringent condition, and encodes a protein having activity for catalyzing hydrolysis of glutamine to glutamic acid and ammonia.

The DNA of the present invention was obtained as described above in the wording examples to be described hereinafter. However, since its nucleotide sequence has been elucidated, it can easily be cloned by PCR, hybridization or the like from genomic DNA of *Aspergillus oryzae* RIB40 (ATCC 42149), *Aspergillus nidulans* A26, or other strains of *Aspergillus oryzae* and *Aspergillus nidulans*.

<3> Use of the DNA of the Present Invention

The DNA of the present invention can be utilized for breeding of filamentous fungi such as koji mould or production of glutaminase. For example, glutaminase activity can be enhanced by intracellularly introducing the DNA of the present invention, preferably as its multiple copies, into filamentous fungus. Glutaminase can be produced by expressing the DNA of the present invention in a suitable host. A filamentous fungus such as koji mould and glutaminase obtained as described above can be utilized for the production of soy sauce, miso, and other seasonings containing protein hydrolysate products.

As the filamentous fungus to be introduced with the DNA of the present invention, there can be mentioned filamentous fungi belonging to the genus *Aspergillus* such as *Aspergillus oryzae*, *Aspergillus niger* and *Aspergillus nidulans*, those belonging to the genus *Neurospora* such as *Neurospora crassa*, those belonging to the genus *Rhizomucor* such as *Rhizomucor miehei*, and the like.

The vector for introducing the DNA of the present invention into filamentous fungi such as those mentioned above is not particularly limited, and those usually used for the breeding of filamentous fungi and the like can be used. As those used for *Aspergillus oryzae*, there can be mentioned, for example, pUNG (Lee, B. R. et al., Appl. Microbiol. Biotechnol., 44, 425–431 (1995)), pMARG (Tsuchiya, K. et al., Appl. Microbiol. Biotechnol., 40, 327–332 (1993)), pUSC (Gomi, K. et al., Agric. Biol. Chem. 51, 2549–2555 (1987)) and the like. pUNG contains a marker complementing niaD$^{31}$ (nitrate assimilation ability defficiency) of *Aspergillus oryzae* niaD300 (Minetoki, T. et al., Curr. Genet. 30, 432–438 (1996)), pMARG contains a marker complementing argB$^{31}$ (arginine auxotroph) of *Aspergillus oryzae* M2-3 (Gomi, K. et al., Agric. Biol. Chem., 51(9), 2549–2555 (1987)), and pUSC contains a marker complementing sC$^{31}$ (ATP sulfurylase defficiency) of *Aspergillus oryzae* NS4 (Yamada, O. et al., Biosci. Biotech. Biochem., 61(8), 1367–1369 (1997))

Among these vectors, pUNG and pMARG contain a promoter of glucoamylase gene (glaA) and α-amylase gene (terminator of amyB), and the DNA of the present invention (region of the nucleotide numbers 1136–4777 or 1177–4777 in SEQ ID NO: 1) can be expressed in them under the control of the promoter to produce glutaminase by inserting the DNA into them in the downstream of the promoter in such a manner that the frames should be conformed. When pUSC is used, because pUSC does not contain a promoter, expression of the gene of the present invention can be obtained by introducing a plasmid such as pUC19 inserted with the DNA of the present invention and pUSC into a host filamentous fungus through co-transformation of them. Since the nucleotide sequences of SEQ ID NO: 1 is likely to contain a promoter as described hereinbefore, it is considered that glutaminase can be expressed even if the DNA of the present invention is inserted into the aforementioned vector together with a promoter.

Those vectors, promoters and markers described in the literature mentioned below can also be used depending on the host filamentous fungus. In Table 2, promoters are indicated by the enzyme names encoded by corresponding genes.

TABLE 2

| Literature | Promoter | Marker | Host filamentous fungus |
|---|---|---|---|
| International Patent Application Publication in Japanese (KOHYO) No. Hei 4-503450/1992 | Neutral α-amylase | | *Aspergillus niger* |
| | | argB | *Aspergillus niger* |
| | | argB | *Aspergillus* |

TABLE 2-continued

| Literature | Promoter | Marker | Host filamentous fungus |
|---|---|---|---|
| | | | *nidulans* |
| | | trpC | *Aspergillus nidulans* |
| | | amdS | *Aspergillus nidulans* |
| | | pyr4 | *Neurospora crassa* |
| | | DHFR | *Neurospora crassa* |
| Japanese Patent Unexamined Publication (KOKAI) No. Sho 62-272988/1987 | Taka-amylase | | *Aspergillus oryzae* |
| | Aspartic protease | | *Rhizomucor miehei* |
| | Lipase | | *Rhizomucor miehei* |
| | Glucoamylase, lipase Amylase, glucoamylase, cellulase Protease, glycolytic pathway enzymes | | *Aspergillus niger* |
| Japanese Patent Unexamined Publication No. Hei 7-51067/1995 | Taka-amylase | | Genus *Aspergillus* |
| Japanese Patent Unexamined Publication No. Hei 7-115976/1995 | Novel promoter sequence is mentioned. | | *Aspergillus oryzae* |
| Japanese Patent Unexamined Publication No. Hei 7-59571/1995 | Novel promoter sequence is mentioned. | | *Aspergillus niger* |
| Journal of Japan Society for Bioscience, Biotechnology and Agrochemistry, Vol. 71, No. 10 (1997) 1018–1023 | α-amylase (amyB) | | *Aspergillus oryzae* |
| | Glucoamylase (glaA) | | *Aspergillus oryzae* |
| | Glucosidase (agdA) | | *Aspergillus oryzae* |

Transformation of filamentous fungi can be performed by the methods mentioned in the aforementioned literature as well as other known methods. Specifically, *Aspergillus oryzae* for example, can be transformed as follows.

Fungal cells (conidiospores) are inoculated in DPY culture medium (2% glucose, 1% peptone, 0.5% yeast extract, pH 5.0), and cultured at 30° C. for around 24 hours with vigorous shaking. The culture medium is filtered through Myracloth (CALBIO CHEM), sterilized gauze or the like to collect the fungal cells, the cells are washed with sterilized water, and moisture is sufficiently removed from the cells. The cells are transferred into a test tube, added with an enzyme solution (1.0% Yatalase (Takara Shuzo), or 0.5% Novozyme (Novo Nordisk) and 0.5% cellulase (e.g., Cellulase Onozuka, Yakult), 0.6 M $(NH_4)_2SO_4$, 50 mM malic acid, pH 5.5), and gently shaken at 30° C. for around 3 hours. The degree of protoplastization is observed with a microscope, and they are stored on ice if they show good protoplastization.

The aforementioned enzymatic reaction mixture is filtered through Myracloth to remove the fungal cell residue, and the filtrate containing protoplasts is added with an equal volume of Buffer A (1.2 M sorbitol, 50 mM $CaCl_2$, 35 mM NaCl, 10 mM Tris-HCl, pH 7.5), and placed on ice. The mixture is centrifuged at 0° C. and 2,500 rpm for 8 minutes, and gently stopped, and the pellet is washed with Buffer A, and suspended in an optimum volume of Buffer A.

A DNA solution of not more than 20 μl (5–10 μg) is added to 100–200 μl of the protoplast suspension, and placed on ice for 20–30 minutes. To the mixture, 250 µl of Buffer B (polyethylene glycol 6000, 50 mM CaCl$_2$, 10 mM Tris-HCl, pH 7.5) is added and gently mixed, again 250 µl of Buffer B is added and gently mixed, further 850 µl of Buffer B is added and gently mixed, and then the mixture is left stand at room temperature for 20 minutes. Then, 10 ml of Buffer A is added to the mixture, and the test tube is inverted and subjected to centrifugation at 0° C. and 2,000 rpm for 8 minutes. Subsequently, the pellet is suspended in 500 µl of Buffer A.

A suitable amount of the above suspension is added to 5 ml top agar, which has been divided into fractions and warmed beforehand, overlaid on an under layer culture medium (selection medium containing 1.2 M sorbitol, which is prepared depending on the kind of marker), and cultured at 30° C. Grown fungal cells are transferred on the selection medium, and confirmed to be transformants. Recombinant DNA is prepared from the fungal cells. It is preferable to confirm that the DNA of the present invention is introduced into the recombinant DNA by restriction enzyme analysis, Southern analysis or the like.

When the transformants obtained as described above are cultured under a condition suitable for the promoter used, the glutaminase gene is expressed, and thus glutaminase is produced.

By allowing a culture of transformants that are introduced with the gene of the present invention and have enhanced glutaminase activity to react with protein, protein hydrolysis products having higher sodium glutamate content and stronger umami can be afforded. Examples of the protein to be reacted with the culture include, for example, those of soybean, wheat, wheat gluten and the like, and it may be those of defatted soybean, or any one of various proteins subjected to food processing such as swelling and solubilization, or proteins isolated from these various kinds of materials.

As for the condition of the reaction of the culture of transformants with the protein, for example, a starting material having a concentration of 0.2–50% may be mixed with a culture of transformants in the presence of a proteolytic enzyme, and allowed to react at 5–60° C. for 4 hours to 10 days.

After the completion of the reaction, insoluble unreacted proteins, fungal cells and the like can be removed by using conventional separation methods such as centrifugal separation or filtration. If required, the reaction mixture may be concentrated by vacuum concentration, reverse osmosis or the like, and the concentrate can be made into powder or granules by a drying process such as lyophilization, drying under reduced pressure, and spray drying. Thus, protein hydrolysates having high sodium glutamate content, and exhibiting stronger umami can be obtained without externally adding sodium glutamate.

DESCRIPTION OF PREFERRED EMBODIMENTS

The present invention will be explained more specifically with reference to the following examples hereinafter.

EXAMPLE 1

Purification of Glutaminase from *Aspergillus oryzae*

Aspergillus oryzaeRIB40 (ATCC 42149) strain was cultured with wheat bran, and glutaminase was purified from the culture. In the purification step, glutaminase activity was determined by a modified version of the method of Hartman (Hartman, S. C., J. Biol. Chem., 243, 853–863 (1968), the hydroxamate method). That is, to 125µ of a solution containing 200 mM Tris-HCl (pH 7.0), 100 mM hydroxylamine hydrochloride, 50 mM L-glutamine, and 10 mM reduced glutathione, 25 µl of enzyme solution was added, and kept at 37° C. for 1 hour. Then, the mixture was added with 125 µl of a solution composed of a mixture of equal volumes of 3 N hydrochloric acid, 12% trichloroacetic acid solution and 5% FeCl$_3$.6H$_2$O solution (dissolved in 0.1 N HCl), and absorption of the mixture at 525 nm was measured. As for the activity, the enzymatic activity which forms 1 µmol of L-glutamic acid γ-monohydroxamate at 37° C. per minute was defined as 1 unit.

(1) Cultivation

Wheat bran (Nisshin Flour Milling, 600 g), potassium phosphate (12 g), and distilled water (600 ml) were mixed well, introduced into six sets of deep Petri dish having a diameter of 15 cm in an amount of 160 g each, and autoclaved at 120° C. for 20 minutes to prepare culture medium.

To a slant culture of *Aspergillus oryzae* RIB40 (ATCC 42149) sufficiently forming spores, sterilized water (5 ml) was poured, and stirred to prepare a spore suspension. The suspension was inoculated to the above culture medium. The culture medium inoculated with the spores was mixed well, and cultured at 30° C. for 14 days. The culture medium was cared by stirring at 24 hours from the beginning of the cultivation.

(2) Extraction of Enzyme

The bran koji prepared as described above was immersed in three-fold volume of 20 mM potassium phosphate buffer (pH 7.4), 1 mM PMSF (phenylmethanesulfonyl fluoride), 0.1 mM EPNP (1,2-epoxy-3-(p-nitrophenyxy)propane), 1 mM EDTA, left stand at 4° C. for 16 hours, and subjected to filtration through gauze and centrifugal separation (4° C., 7,500 rpm for 30 minutes) to afford a supernatant, which was used as a crude enzyme extract.

(3) Fractionation by Ammonium Sulfate Precipitation

The crude enzyme extract was frozen at –80° C., and gradually thawed at 4° C., and insoluble fractions were removed by filtration. The resultant was added with ammonium sulfate (1010 g/2,880 ml) to afford a 55% saturated ammonium sulfate solution. The solution was stirred at 40° C. for 4 hours, and centrifuged (4° C., 7,500 rpm, 30 minutes) to remove the precipitates. The supernatant was further added with ammonium sulfate (703 g/3,180 ml) to afford an 85% saturated ammonium sulfate solution. The solution was stirred at 4° C. for 16 hours, and the produced precipitates were collected by centrifugation (4° C., 7,500 rpm, 30 minutes), and dissolved in 100 ml of 20 mM sodium phosphate buffer (pH 7.4). This was filtered through a filter having a pore diameter of 0.45 µm.

(4) Desalination 5 ml from 100 ml of the filtrate obtained in the above (3) was loaded on a column for desalination which had been preliminarily equilibrated with 20 mM potassium phosphate buffer (pH 7.4), 100 mM NaCl beforehand (HiTrap Desalting, Pharmacia, 5 ml×5), and eluted wish the same buffer solution. This desalination procedure was performed 20 times each for 5 ml divided from 100 ml of the filtrate. The active fractions were combined to amount 300 ml, and concentrated and desalted to 50 ml by ultrafiltration.

(5) Anion Exchange Chromatography

The sample obtained above was adsorbed on a column filled with 250 ml DEAE-TOYOPEARL 650M (Tosoh), which had been preliminarily equilibrated with 20 mM potassium phosphate buffer (pH 7.4), and washed with the same buffer solution in a 4-fold volume of the column volume. After the washing, the column was eluted with linear gradient of NaCl increasing from 0 M to 0.5 M in the buffer of 8-fold volume of the column volume. The active fractions collected in the eluent (340 ml) was concentrated and desalted to 12 ml by ultraliltration.

(6) Hydrophobic Chromatography

Then, fractionation by absorption chromatography was performed on a FPLC system (Pharmacia) utilizing HiLoad 26/10 Phenyl Sepharose High Performance (Pharmacia). This chromatographic procedure was performed twice for divided portions of the protein of DEAE-TOYOPEARL active fraction. 6 ml of the DEAE-TOYOPEARL active fraction added with 1 M ammonium sulfate was adsorbed on the column preliminarily equilibrated with 50 mM sodium phosphate buffer (pH 7.4), and 1 M ammonium sulfate, and the column was washed with the same buffer solution of 4-fold volume of the column volume. After the washing, the column was eluted with the buffer solution having linear ammonium sulfate gradient decreasing from 1 M to 0 M in 16-fold volume of the column volume. 300 ml of active fraction from the eluent was concentrated and desalted to 10 ml by ultrafiltration and centrifugal concentration (Centriprep 10, AMICON).

(7) Gel Filtration Chromatography

The above sample was subjected to fractionation by gel filtration chromatography on a FPLC system utilizing HiLoad 26/60 Superdex 200 pg (Pharmacia). This chromatographic procedure was performed 5 times for divided portions from the protein of the DEAE-TOYOPEARL active fraction. 2 ml of the active fraction obtained above was loaded on the column preliminarily equilibrated with 40 mM sodium phosphate buffer (pM 7.4), and 150 mM NaCl, and the column was eluted with the same buffer to collect active fraction. This gel filtration chromatography was repeated twice.

(8) Results of Purification

By the above-mentioned purification process, 500 µg of purified glutaminase was obtained. The molecular weight of the purified enzyme was determined by MALDI-TOFMS (Matrix assisted laser desorption ionization-time of flight mass spectrometer), and it was found to be 8,290. Total protein, total activity, specific activity, yield, and purity (based on the purity of the crude enzyme extract that was defined as 1) in various purification steps are summarized in Table 3.

TABLE 3

| Purification step | Glutaminase activity (Unit) | Amount of protein (mg) | Specific activity (unit/mg) | Yield (%) | Purity (fold) |
|---|---|---|---|---|---|
| Crude extract | 44.8 | 2528 | 0.018 | 100 | 1 |
| Freeze-thawing | 51 | 2230 | 0.023 | 114 | 1.28 |
| Ammonium sulfate precipitation | 16.2 | 665 | 0.024 | 36 | 1.33 |
| DEAE-TOYOPEARL | 7.2 | 186 | 0.039 | 16 | 2.2 |
| Phenyl Sepharose | 4.3 | 78.7 | 0.055 | 9.6 | 3.1 |
| First gel filtration | 0.8 | 1.1 | 0.73 | 1.6 | 39.4 |
| Second gel filtration | 0.4 | 0.5 | 0.88 | 1 | 48.9 |

(9) Determination of Partial Amino Acid Sequence or Glutaminase

The purified glutaminase (97 µg) in 500 mM Tris hydrochloric acid (pH 8.1), 6 M guanidine, and 2 mM EDTA was added with DTT (263 µg), substituted with nitrogen, and kept at 50° C. for 3 hours. The reduction reaction was performed at room temperature overnight while the reaction mixture was shielded from light. The mixture was further added with iodoacetic acid (2900 µg), allowed to react at room temperature for 30 minutes, and desalted on a Sephadex G-25 (Pharmacia) column. The desalted sample was concentrated on centrifugal concentration machine VC-960 (TAITEC), and added with 50 mM ammonium hydrogencarbonate (pH 8.5) and 1 µg lysyl endopeptidase (SIGMA) to perform limited degradation at 37° C. for 13 hours. After the reaction, the produced peptides were isolated by reversed-phase HPLC (Vydac Capillary $C_{18}$, Vydac), and each subjected to sequencing on a peptide sequencer PPSQ-10 (Shimazu Corporation) to determine internal partial amino acid sequences or glutaminase. Separately, the peptide not undergone the lysyl endopeptidase treatment was also subjected to sequencing on the peptide sequencer to determine its N-terminal amino acid sequence. The determined amino acid sequences are listed below.

N-terminal: ASTFSPARPPALPLAVK (SEQ ID NO: 3)
No. 52: Y(G/P)(N/V)(T/P)YAM(R/S)DI (SEQ ID NO: 4)
No. 55: VQY(T/G)EYDXY (SEQ ID NO: 5)
No. 59: DNDYLSQHYPILNK (SEQ ID NO: 6)
No. 67: WTAYLVEDTIYPANQ (SEQ ID NO: 7)
No. 62.5: VLLQSAIEGH (SEQ ID NO: 8)
No. 63: GIIGIQAMAV (SEQ ID NO: 9)
No. 62: XILKFXYXXQ (SEQ ID NO: 10)

In the aforementioned sequences, "X" represents an indefinite amino acid, and "/" means that the corresponding amino acid is one indicated before or after it.

EXAMPLE 2

Cloning of Glutaminase Gene of *Aspergillus oryzae*

The glutaminase gene was isolated from a genomic library of *Aspergillus oryzae* by plaque hybridization.

(1) Production of Probe by PCR

From cells of *Aspergillus oryzae* RIB40, genome DNA was prepared as follows according to the method of Gomi (Gomi, K. et al., J. Gen. Appl. Microbiol., 35, 225 (1989))

Spores of *Aspergillus oryzae* RIB40 from two slant culture tubes were suspended in 0.85% NaCl, inoculated in 1 L of YPD culture medium (2% glucose, 1% peptone, 0.5% yeast extract, pH 5.0), and cultured at 30° C. for 24 hours. The fungal cells were collected by filtration through gauze, immediately frozen with liquid nitrogen, and disrupted in a homogenizer (18000 rpm, 15 minutes) while cooling with liquid nitrogen or in a mortar. The resultant was added with 100 ml of 50 mM EDTA, 0.5% SDS, pH 8.0, and proteinase K to a final concentration of 0.1 mg/ml, and incubated at 50° C. for 4 hours. This solution was subjected to phenol treatment, phenol/chloroform treatment, and chloroform treatment twice each. These treatments with organic solvents were performed by gently mixing the solution and the organic solvents, and separating an aqueous layer.

The solution from which the protein had been removed as described above was added with 1/10 volume of 3 M sodium acetate (pH 5.2) and 2.5-fold volume of ethanol, left at −20° C. overnight, and centrifuged at 0° C. and 10,000 rpm for 20 minutes. The resulting precipitates were rinsed, and carefully dissolved in TE buffer. This solution was added with RNase A (10 µg/ml), and incubated at 37° C. for 30 minutes to degrade RNA. Then, the solution was mixed with ½ volume of phenol, left at 37° C. for 10 minutes, mixed with ½ volume of chloroform, and centrifuged at 0° C. and 10,000 rpm for 20 minutes to separate the aqueous layer. This aqueous layer was mixed with diethyl ether, and centrifuged at 0° C. and 10,000 rpm for 5 minutes, and the diethyl ether layer was removed to eliminate the phenol remained in the solution. The resulting aqueous layer was added with 3 M sodium acetate solution (500 μl) and ethanol (5 ml), left at −80° C. for one hour, and centrifuged at 10,000 rpm for 20 minutes to afford precipitates. These precipitates were rinsed, dissolved in TE buffer (5 ml), added with a small amount of chloroform, and stored under refrigeration.

After PCR using the genome DNA obtained as described above as template, and oligonucleotides which were synthesized based on the partial amino acid sequences (No. 52 and No. 67) and had the following sequences as primers, a partial sequence of glutaminase gene was obtained, and this was used as a probe for hybridization. The sequences of these primers were designed by referring to the codon frequency of *Aspergillus nidulans* (Andrew, T. Lloyd et al., Mol. Gen. Genet., 230, 288–294 (1991)).
(5' end primer)
TAC CCC AAC ACC TAT GCT ATG CGC GAT ATC (SEQ ID NO: 11)
(3' end primer)
TTG GTT CGC CGG ATA AAT AGT ATC TTC CAC CAA GTA (SEQ ID NO: 12)

The PCR reaction was performed by heat-denaturation at 95° C. for 9 minutes, and a cycle of 94° C. for 1 minute, 53° C. for 1 minute, and 72° C. for 1.5 minutes, which cycle was repeated for 35 cycles. This provided an about 230 b glutaminase gene fragment.

(2) Screening of *Aspergillus oryzae* Genomic Library

Screening of *Aspergillus oryzae* genomic library was performed by using the gene fragment obtained in the above PCR reaction as a probe.

The *Aspergillus oryzae* genome DNA was digested with BamHI into about 10 kb fragments, and they were inserted into BamHI site of λ phage vectors (λ DASH II, STRATAGENE). The obtained recombinant DNAs were in vitro packaged to construct a λ phage library.

Using the aforementioned λ phage library, about 5,000 plaques were formed per one plate having a diameter of 15 cm. Ten plates on which plaques were formed were prepared, and each plate was blotted to two pieces of nylon membranes (Hybond-N+, Amersham). That is, the nylon membranes were placed on the plate for 3 minutes for the first piece, or for 5 minutes for the second piece, and then placed on filter paper sheets soaked with a denaturation solution (1.5 M NaCl, 0.5 M NaOH) for 7 minutes. Then, the membranes were placed on filter paper sheets soaked with a neutralization solution (1.5 M NaCl, 0.5M Tris-HCl (pH 7.4)) for 3 minutes, and then on other filter paper sheets soaked with the same buffer for 3 minutes for neutralization, left stand in 2×SSC for 3 minutes, and air-dried. After the drying, the membranes were placed on filter paper sheets soaked with 0.4 M NaOH for 20 minutes, shaken in 5×SSC for 1 minute, and air-dried.

Each of the nylon membranes mentioned above was immersed into a pre-hybridization buffer (50% formamide, 5× Denhardt's solution, 5×SSPE, 0.5% SDS), and kept at 42° C. for 2 hours. The probe obtained in the PCR was labeled with [$^{32}$P-γ]-CTP using Random Label Kit (BOEHRINGER MANNHEIM). The labeled probe was kept at 100° C. for 3 minutes, immediately transferred on ice so that the DNA double strands should be denatured, and added to the pre-hybridization buffer, and the hybridization was performed at 42° C. overnight.

The aforementioned nylon membrane was subjected to washing in 2×SSC, 0.1% SDS at 65° C. for 15 minutes twice, washing in 1×SSC, 0.1% SDS at 65° C. for 15 minutes twice, and washing in 0.1×SSC, 0.1% SDS at 65° C. for 15 minutes twice. After the washing, the membrane was brought into contact with an imaging plate (FUJIX), and detected with an image analyzer BAS2000 (FUJIX). As a result, 21 positive signals were detected from about 50,000 plaques.

The 21 positive plaques were collected, and subjected to the second screening. In the second screening, about 50 plaques were formed on a plate having a diameter of 10 cm, and hybridization was performed in the same manner as in the first screening. Four kinds of positive plaques were detected in the second screening. The third screening was performed in the same manner as in the second screening, and four kinds of positive clones were finally obtained.

Nucleotide sequencing of these four kinds of clones revealed that all of the clones contained the same sequence. The nucleotide sequence of XhoI fragment derived from one of the clones, and the amino acid sequence encoded by the nucleotide sequence are shown in SEQ ID NO: 1 The amino acid sequence alone is shown in SEQ ID NO: 2.

*Escherichia coli* DH5 α strain which had been transformed with a plasmid obtained by inserting the aforementioned XhoI fragment into plasmid pBluescript was given a private number of AJ13495, and it was deposited at the National Institute of Bioscience and Human-Technology, Agency of Industrial Science and Technology, Ministry of International Trade and Industry (zip code: 305-8566, 1-3 Higashi 1-Chome, Tsukuba-shi, Ibaraki-ken, Japan) on Sep. 9, 1998, and received an accession No. FERM BP-6490.

EXAMPLE 3

Cloning of Glutaminase cDNA of *Aspergillus oryzae*

A highly glutaminase productive strain of *Aspergillus oryzae* was cultured in DPY culture medium (50 ml) at 30° C. for 48 hours. The fungal cells were collected by filtration through gauze to obtain 1 g of cells. The cells were immediately frozen with liquid nitrogen, and disrupted in a mortar, from which 0.2 mg of total RNA were obtained according to the guanidine-cesium chloride ultracentrifugation method (Molecular Cloning, 2nd edition, Cold Spring Harbor Press (1989)). From the total RNA, mRNA was purified by using mRNA Purification Kit (Pharmacia), and cDNA Was synthesized with cDNA PCR Library Kit (Takara Shuzo). By using this kit, a CA cassette adapter sequence is ligated to the 5' end of the obtained cDNA, and an oligo dT-RA sequence to the 3' end.

By using the cDNA obtained as described above as template, and oligonucleotides synthesized based on the nucleotide sequence of glutaminase genome and having the following sequences as primers, the glutaminase cDNA was amplified by PCR and 3'-RACE.
(5' end primer)
GAT CAT GAT GCA TTT CCT CTC GTT CTG TC (SEQ ID NO: 13)
(3' end primer)
GCA AAG TCA TCC GTA GAG ATC TGG TTC G (SEQ ID NO: 14)
(5' end primer for 3'-RACE)
GGC GAA CCA GAT CTC TAC GGA TGA CTT TGC (SEQ ID NO: 15)
(3' end primer for 3'-RACE)
CTG ATC TAG ACC TGC AGG CTC (SEQ ID NO: 16)

The PCR reactions were each performed by heat-denaturation at 95° C. for 9 minutes, and a cycle of 94C for 1 minute, 55° C. for 1 minute, and 72° C. for 1 minute, which cycle was repeated for 30 cycles. The PCR using the primers of SEQ ID NOS: 13 and 14 provided an about 1500 bp DNA fragment, and the 3'-RACE using the primers of SEQ ID NOS: 15 and 16 provided an about 780 bp DNA fragment.

The nucleotide sequence of these DNA fragments is shown in SEQ ID NO: 17. The amino acid sequence deduced from this nucleotide sequence is shown in SEQ ID NOS: 17 and 18.

EXAMPLE 4

Expression of Glutaminase cDNA in *Escherichia coli*

Lac promoter, T7 promoter or Trp promoter is ligated to the upstream of the glutaminase cDNA., and inserted into a multi-cloning site of pBluescript (Stratagene). *Escherichia coli* DH5α is transformed with the obtained recombinant plasmid in a conventional manner, and the obtained transformants are selected on an agar medium containing 50 μg/ml of ampicillin. The selected transformants are cultured at 37° C. in LB culture medium (1% trypton, 0.5% yeast extract, 1% NaCl) overnight This culture medium (1 ml) is transferred into LB culture medium (50 ml), and cultured at 37° C. When its OD reaches 0.6 after 3 hours, IPTG (isopropyl-β-D-thiogalactopyranoside) is added to a final concentration of 1 mM to induce lac promoter, and the cultivation at 37° C. is further continued for 4 hours. After the cultivation, the cells are collected, suspended in a buffer, and sonicated to provide protein inclusion bodies. These inclusion bodies are dissolved in a denaturant solution (8 M urea, 10 mM DTT, 50 mM NaCl, 50 mM Tris-HCl (pH 8.0), 5 mM EDTA), and insoluble fractions are removed by centrifugation. Refolding of the protein can be achieved by gradually lowering the urea concentration in the solution of solubilized protein.

*Escherichia coli* DH5α strain which had been transformed with a plasmid obtained by inserting the aforementioned glutaminase cDNA fragment into plasmid pbluescript was given a private number of AJ13496, and it was deposited at the National Institute of Bioscience and Human-Technology, Agency of Industrial Science and Technology, Ministry of International Trade and Industry (zip code: 305-8566, 1-3 Higashi 1-Chome, Tsukuba-shi, Ibaraki-ken, Japan) on Sep. 9, 1998, and received an accession No. FERM BP-6491.

EXAMPLE 5

Cloning of Glutaminase Gene of *Aspergillus nidulans*

(1) Production of Probe by PCR

Based on the nucleotide sequence of the glutaminase gene of *Aspergillus oryzae* determined in Examples 1 and 2, oligonucleotide primers for PCR were synthesized, and PCR was performed by using genome DNA prepared from cells of *Aspergillus nidulans* A26 as template. The genome DNA was prepared in the same manner as in Example 2 according to the method of Gomi (Gomi, K. et al., J. Gen. Appl. Microbiol., 35, 225(1989)).

Oligonucleotides having sequences of the nucleotide numbers 1952–1979 and 2839–2868 of SEQ ID NO: 1 in Sequence Listing were synthesized as the PCR primers.
(5' end primer)
GAC GAC CAA GAT GGT CTG AGC TAC CAG T (1952–1979) (SEQ ID NO: 19)
(3' end primer)
GCA AAG TCA TCC GTA GAG ATC TGG TTC GCC (2839–2868) (SEQ ID NO: 20)

The PCR reaction was performed by heat-denaturation at 95° C. for 3 minutes, and a cycle of 94° C. for 1 minute, 37° C. for 1 minute, and 72° C. for 1 minute, which cycle was repeated for 30 cycles. This provided an about 900 b glutaminase gene fragment.

(2) Screening of *Aspergillus nidulans* Genomic Library

Screening of *Aspergillus nidulans* genomic library was performed by using the gene fragment obtained in the above PCR reaction as a probe.

The *Aspergillus nidulans* genomic library was purchased from Fungal Genetics Strain Center (Kansas City, USA). Using this library, agar medium was prepared in a plate having a diameter of 10 cm, and a nylon membrane Hybond-N+ (Amersham) was overlaid thereon. The cells were inoculated on the nylon membrane to form about 50 colonies on one membrane. 30 pieces of plate on which the colonies were formed were prepared, and a nylon membrane was collected from each plate. Each nylon membrane was placed on a filter paper sheet soaked with a denaturation solution (1.5 M NaCl, 0.5 M NaOH) for 7 minutes. Then, the membrane was placed on a filter paper sheet soaked with a neutralization solution (1.5 M NaCl, 0.5M Tris-HCl (pH 7.4)) for 3 minutes, and then on another filter paper sheet soaked with the same buffer for 3 minutes for neutralization, left stand in 2×SSC for 3 minutes, and air-dried. After the drying, the membrane was placed on a filter paper sheet soaked with 0.4 M NaOH for 20 minutes, shaken in 5×SSC for 1 minute, and air-dried.

The nylon membrane mentioned above was soaked into a pre-hybridization buffer (50% formamide, 5× Denhardt's solution, 5×SSPE, 0.5% SDS), and kept at 65° C. for 2 hours. The probe obtained in the PCR was labeled with [$^{32}$P-γ]-CTP using Random Label Kit (BOEHRINGER MANNHEIM). The labeled probe was kept at 100° C. for 3 minutes, immediately transferred on ice so that the DNA double strands should be denatured, and added to the pre-hybridization buffer, and the hybridization was performed at 65° C. overnight.

The aforementioned nylon membrane was subjected to washing in 2×SSC, 0.1% SDS at 65° C. for 15 minutes twice, washing in 1×SSC, 0.1% SDS at 65° C. for 15 minutes twice, and washing in 0.1×SSC, 0.1% SDS at 65° C. for 15 minutes twice. After the washing, the membrane was brought into contact with an imaging plate (FUJIX), and detected with an image analyzer BAS2000 (FUJIX). As a result, 4 positive signals were detected from about 1500 colonies.

Nucleotide sequencing of these four kinds of clones revealed that all of the clones contained the same sequence. The nucleotide sequence of HindIII-EcorRV fragment derived from one of the clones, and the amino acid sequence encoded by the nucleotide sequence are shown in SEQ ID NO: 21. The amino acid sequence alone is shown in SEQ ID NO: 22.

*Escherichia coli* DH5α strain which had been transformed with a plasmid obtained by inserting the aforementioned HindIII-EcorRV fragment into plasmid pBluescript was given a private number of AJ13509, and it was deposited at the Fermentation Research Institute, Agency of Industrial Science and Technology, Ministry of International Trade and Industry (currently the National Institute of Bioscience and Human-Technology, Agency of Industrial Science and Technology, Ministry of International Trade and Industry) on Sep. 22, 1998, and received an accession No. FERM BP-6520.

EXAMPLE 6

Cloning of Glutaminase cDNA of *Aspergillus nidulans*

*Aspergillus nidulans* A26 was cultured in 50 ml of YG culture medium (0.5% yeast extract, 2.5% glucose, 0.1% trace elements*) at 37° C. for 21 hours with shaking. The cells were collected on a filter paper sheet, and cultured in a plate containing minimal medium (0.6% $NaNO_3$, 0.152% $KH_2PO_4$, 0.052% KCl, 0.052% $MgSO_4.7H_2O$, 1% glucose, 0.1% trace elements*, $2\times10^{-5}$% biotin, 1.5% agar) at 37° C. for 24 hours (trace elements*: 0.1% $FeSO_4.7H_2O$, 0.88% $ZnSO_4.7H_2O$, 0.04% $CuSO_4.5H_2O$, 0.015% $MnSO_4.4H_2O$, 0.01% $Na_2B_4O_7.10H_2O$, 0.005% $(NH_4)_6Mo_7O_{24}.4H_2O$).

The cells were collected from the plate, frozen with liquid nitrogen, and disrupted in a mortar. Total RNA was prepared using RNeasy Plant Mini Kit (QIAGEN) from the disrupted product, and mRNA was prepared from the total RNA using mRNA Purification Kit (Amersham Pharmacia Biotech). A cDNA library was prepared from the mRNA using cDNA Synthesis Kit and cDNA PCR Library Kit (Takara).

By using the cDNA library as template, and the following primers which had been designed based on the *Aspergillus nidulans* genomic DNA sequence, cloning of glutaminase cDNA was performed by PCR.
(5' end primer)
GCT TCA TAA TTC TCC TGT TGT TGA GTC (SEQ ID NO: 23) Anti-sense primer
(3' end primer)
GGC TAT AAC TGA TGC TAT ATA CTA CCA CAC (SEQ ID NO: 24)

The reactions of the PCR were performed by heat denaturation at 94° C. for 5 minutes, and 30 cycles of [94° C. for 30 seconds, 55° C. for 30 seconds, 72° C. for 2 minutes]. As a result, an amplified fragment of about 2300 bp was observed, and thus a full length glutaminase cDNA was successfully obtained. The nucleotide sequence of this DNA fragment is shown in SEQ ID NO: 25. The amino acid sequence deduced from this nucleotide sequence is shown in SEQ ID NO: 26.

*Escherichia coli* DH5α0 strain which had been transformed with a plasmid obtained by inserting the aforementioned *Aspergillus nidulans* glutaminase cDNA fragment into TA cloning site of pGEM T Easy Vector (Promega) was given a private number of AJ13575, and it was deposited at the National Institute of Bioscience and Human-Technology, Agency of Industrial Science and Technology, Ministry of International Trade and Industry (zip code: 305-8566, 1-3 Higashi 1-Chome, Tsukuba-shi, Ibaraki-ken, Japan) on March 11, 1999, and received an accession No. FERM BP-6679.

EXAMPLE 7

Production of Glutaminase

The glutaminase gene containing a promoter sequence was ligated to a vector containing a marker gene sC to provide a vector for transformation. Transformation was performed by using 10 µg of this plasmid DNA.

Conidiospores were inoculated in DPY culture medium, and cultured at 30° C. for 24 hours with vigorous shaking. The culture medium was filtered through sterilized gauze, the cells were collected, and washed with sterilized water, and moisture was sufficiently removed from the cells. These cells were transferred to a test tube, added with an enzyme solution (20 ml, 1.0% Yatalase, Takara Shuzo), and gently shaken at 30° C. for 3 hours. The degree of protoplastization was observed with a microscope, and they are stored on ice.

The aforementioned enzymatic reaction mixture was filtered through Myracloth to remove the cell residue, and the filtrate containing protoplasts was added with an equal volume of Buffer A (1.2 M sorbitol, 50 mM $CaCl_2$, 35 mM NaCl, 10 EM Tris-HCl, pH 7.5), and placed on ice. The mixture was centrifuged at 0° C. and 1,500 rpm for 5 minutes, and gently stopped, and the pellet was washed with Buffer A twice, and suspended in 1 ml of Buffer A.

A DNA solution (10 µl, 10 µg) was added to 100 µl of the protoplast suspension, and placed on ice for 30 minutes. To the mixture, 250 µl of Buffer B (60% PEG (polyethylene glycol) 6000, 50 mM $CaCl_2$, 10 mM Tris-HCl, pH 7.5) was added and gently mixed, then 250 µl of Buffer B was added again and gently mixed, and 850 µl of buffer B was further added and gently mixed, and the mixture was left stand at room temperature for 20 minutes. Then, 10 ml of Buffer A was added to the mixture, and the test tube was inverted and subjected to centrifugation at 0° C. and 1,500 rpm for 5 minutes. Then, the pellet was suspended in 500 µl of Buffer A.

The above suspension was added to 5 ml top agar culture medium, which had been divided into fractions and warmed beforehand, overlaid on M culture medium (1.2 M sorbitol, 0.2% ammonium chloride, 0.1% ammonium sulfate, 0.05% potassium chloride, 0.05% sodium chloride, 0.1% potassium dihydrogenphosphate, 0.05% magnesium at 4° C. for 16 hours, and subjected to filtration through gauze and centrifugal separation (4° C., 15 minutes, 10,000 rpm) to provide a supernatant, which was used as a crude enzyme extract.

The glutaminase activity of this crude enzyme extract was determined. Another crude enzyme extract was similarly obtained from a transformant obtained by transforming a vector DNA having only the marker gene as control, and its glutaminase activity was measured.

TABLE 4

| | Glutaminase activity (per koji mg) |
|---|---|
| Transformant | 1.43 U/mg |
| Control strain | 0.38 U/mg |

As a result, marked activity increase was observed in the strain that had been introduced with the gene of the present invention, and it was demonstrated that the introduced glutaminase was expressed and produced.

INDUSTRIAL APPLICABILITY

The present invention provides a novel gene encoding glutaminase derived from koji mould. This gene can be used for breeding of koji mould, production of glutaminase, and production of seasonings such as soy sauce.

What is claimed is:
1. An isolated DNA, which encodes a protein with glutaminase activity and which hybridizes under stringent conditions to SEQ ID NO: 17, wherein said stringent conditions comprise washing in 0.1×SSC and 0.1% SDS at 65° C. for 15 minutes.
2. A recombinant vector comprising the isolated DNA of claim 1.

3. A transformed microorganism comprising the isolated DNA of claim 1.

4. The transformed microorganism of claim 3 which is of a genus selected from the group consisting of *Escherichia, Aspergillus, Neurospora*, and *Rhizomucor*.

5. The transformed microorganism of claim 3, which is selected from the group consisting of *Aspergillus oryzae, Aspergillus niger, Aspergillus nidulans, Neurospora crassa*, and *Rhizomucor miehei*.

6. A method of producing glutaminase, comprising cultivating the transformed microorganism of claim 3 in a culture medium for a time sufficient to produce glutaminase; and collecting the glutaminase produced.

7. An isolated protein with glutaminase activity encoded by a DNA, which hybridizes under stringent conditions to SEQ ID NO:17, wherein said stringent conditions comprise washing in 0.1×SSC and 0.1% SDS at 65° C. for 15 minutes.

8. An isolated protein comprising amino acids 1–670 of SEQ ID NO:2.

9. An isolated DNA, which encodes the isolated protein of claim 8.

10. A recombinant vector comprising the isolated DNA of claim 9.

11. A transformed microorganism comprising the isolated DNA of claim 9.

12. The transformed microorganism of claim 11, which is of a genus selected from the group consisting of *Escherichia, Aspergillus, Neurospora*, and *Rhizomucor*.

13. The transformed microorganism of claim 11, which is selected from the group consisting of *Aspergillus oryzae, Aspergillus niger, Aspergillus nidulans, Neurospora crassa*, and *Rhizomucor miehei*.

14. A method of producing glutaminase, comprising cultivating the transformed microorganism of claim 11 in a culture medium for a time sufficient to produce glutaminase; and collecting the glutaminase produced.

15. A method of producing glutamic acid, comprising contacting glutamine with the isolated protein of claim 8.

16. A method of producing glutamic acid, comprising contacting glutamine with the transformed microorganism of claim 13.

17. An isolated DNA comprising, the nucleotide sequence of SEQ ID NO:17.

18. A recombinant vector comprising the isolated DNA of claim 17.

19. A transformed microorganism comprising the isolated DNA of claim 17.

20. The transformed microorganism of claim 19, which is of a genus selected from the group consisting of *Escherichia, Aspergillus, Neurospora*, and *Rhizomucor*.

21. The transformed microorganism of claim 19, which is selected from the group consisting of *Aspergillus oryzae, Aspergillus niger, Aspergillus nidulans, Neurospora crassa*, and *Rhizomucor miehei*.

22. A method of producing glutaminase, comprising cultivating the transformed microorganism of claim 19 in a culture medium for a time sufficient to produce glutaminase; and collecting the glutaminase produced.

\* \* \* \* \*